(12) United States Patent
Baril et al.

(10) Patent No.: US 12,383,303 B2
(45) Date of Patent: Aug. 12, 2025

(54) SURGICAL ACCESS DEVICE HAVING PLURAL ZERO CLOSURE VALVES

(71) Applicant: Covidien LP, Mansfield, MA (US)

(72) Inventors: Jacob C. Baril, Norwalk, CT (US); Saumya Banerjee, Hamden, CT (US); Justin Thomas, New Haven, CT (US); Matthew A. Dinino, Newington, CT (US); Roy J. Pilletere, Middletown, CT (US); Nicolette L. Roy, Windsor Locks, CT (US); Garrett P. Ebersole, Hamden, CT (US)

(73) Assignee: Covidien LP, Mansfield, MA (US)

( * ) Notice: Subject to any disclaimer, the term of this patent is extended or adjusted under 35 U.S.C. 154(b) by 417 days.

(21) Appl. No.: 17/093,946

(22) Filed: Nov. 10, 2020

(65) Prior Publication Data
US 2022/0142672 A1 May 12, 2022

(51) Int. Cl.
*A61B 17/34* (2006.01)

(52) U.S. Cl.
CPC ...... *A61B 17/3423* (2013.01); *A61B 17/3474* (2013.01); *A61B 17/3498* (2013.01)

(58) Field of Classification Search
CPC ............ A61B 17/3423; A61B 17/3474; A61B 17/3498; A61B 17/3421
See application file for complete search history.

(56) References Cited

U.S. PATENT DOCUMENTS

| | | |
|---|---|---|
| 397,060 A | 1/1889 | Knapp |
| 512,456 A | 1/1894 | Sadikova |
| 1,213,005 A | 1/1917 | Pillsbury |
| 2,912,981 A | 11/1959 | Keough |
| 2,936,760 A | 5/1960 | Gains |
| 3,039,468 A | 6/1962 | Price |
| 3,050,066 A | 8/1962 | Koehn |
| 3,253,594 A | 5/1966 | Matthews et al. |
| 3,397,699 A | 8/1968 | Kohl |
| 3,545,443 A | 12/1970 | Ansari et al. |
| 3,713,447 A | 1/1973 | Adair |
| 3,774,596 A | 11/1973 | Cook |
| 3,800,788 A | 4/1974 | White |

(Continued)

FOREIGN PATENT DOCUMENTS

| | | |
|---|---|---|
| EP | 0480653 A1 | 4/1992 |
| EP | 0610099 A2 | 8/1994 |

(Continued)

OTHER PUBLICATIONS

The International Search Report and Written Opinion dated Feb. 23, 2022 issued in corresponding PCT Appln. No. PCT/US2021/057967.

*Primary Examiner* — Tracy L Kamikawa
(74) *Attorney, Agent, or Firm* — Draft Masters IP, LLC

(57) ABSTRACT

A surgical access device includes a seal assembly, an upper housing portion, a lower housing portion, and a tubular member. The seal assembly has an instrument seal and is coupled to the upper housing portion. A first valve is partially disposed in an upper chamber of the upper housing portion and a second valve is partially disposed in a lower chamber of the lower housing portion. A valve assembly extends from the upper housing portion and is in fluid communication with the upper chamber. A source of insufflation fluid is attachable to the valve assembly.

20 Claims, 6 Drawing Sheets

(56) References Cited

U.S. PATENT DOCUMENTS

| | | |
|---|---|---|
| 3,882,852 A | 5/1975 | Sinnreich |
| 3,896,816 A | 7/1975 | Mattler |
| 3,961,632 A | 6/1976 | Moossun |
| RE29,207 E | 5/1977 | Bolduc et al. |
| 4,083,369 A | 4/1978 | Sinnreich |
| 4,217,889 A | 8/1980 | Radovan et al. |
| 4,243,050 A | 1/1981 | Littleford |
| 4,276,874 A | 7/1981 | Wolvek et al. |
| 4,312,353 A | 1/1982 | Shahbabian |
| 4,327,709 A | 5/1982 | Hanson et al. |
| 4,345,606 A | 8/1982 | Littleford |
| 4,411,654 A | 10/1983 | Boarini et al. |
| 4,416,267 A | 11/1983 | Garren et al. |
| 4,490,137 A | 12/1984 | Moukheibir |
| 4,496,345 A | 1/1985 | Hasson |
| 4,574,806 A | 3/1986 | McCarthy |
| 4,581,025 A | 4/1986 | Timmermans |
| 4,596,554 A | 6/1986 | Dastgeer |
| 4,596,559 A | 6/1986 | Fleischhacker |
| 4,608,965 A | 9/1986 | Anspach, Jr. et al. |
| 4,644,936 A | 2/1987 | Schiff |
| 4,654,030 A | 3/1987 | Moll et al. |
| 4,685,447 A | 8/1987 | Iversen et al. |
| 4,701,163 A | 10/1987 | Parks |
| 4,738,666 A | 4/1988 | Fuqua |
| 4,769,038 A | 9/1988 | Bendavid et al. |
| 4,772,266 A | 9/1988 | Groshong |
| 4,779,611 A | 10/1988 | Grooters et al. |
| 4,784,133 A | 11/1988 | Mackin |
| 4,793,348 A | 12/1988 | Palmaz |
| 4,798,205 A | 1/1989 | Bonomo et al. |
| 4,800,901 A | 1/1989 | Rosenberg |
| 4,802,479 A | 2/1989 | Haber et al. |
| 4,813,429 A | 3/1989 | Eshel et al. |
| 4,840,613 A | 6/1989 | Balbierz |
| 4,854,316 A | 8/1989 | Davis |
| 4,861,334 A | 8/1989 | Nawaz |
| 4,865,593 A | 9/1989 | Ogawa et al. |
| 4,869,717 A | 9/1989 | Adair |
| 4,888,000 A | 12/1989 | McQuilkin et al. |
| 4,899,747 A | 2/1990 | Garren et al. |
| 4,917,668 A | 4/1990 | Haindl |
| 4,931,042 A | 6/1990 | Holmes et al. |
| 4,955,895 A | 9/1990 | Sugiyama et al. |
| 5,002,557 A | 3/1991 | Hasson |
| 5,009,643 A | 4/1991 | Reich et al. |
| 5,030,206 A | 7/1991 | Lander |
| 5,030,227 A | 7/1991 | Rosenbluth et al. |
| 5,074,871 A | 12/1991 | Groshong |
| 5,098,392 A | 3/1992 | Fleischhacker et al. |
| 5,104,383 A | 4/1992 | Shichman |
| 5,116,318 A | 5/1992 | Hillstead |
| 5,116,357 A | 5/1992 | Eberbach |
| 5,122,122 A | 6/1992 | Allgood |
| 5,122,155 A | 6/1992 | Eberbach |
| 5,137,512 A | 8/1992 | Burns et al. |
| 5,141,494 A | 8/1992 | Danforth et al. |
| 5,141,515 A | 8/1992 | Eberbach |
| 5,147,302 A | 9/1992 | Euteneuer et al. |
| 5,147,316 A | 9/1992 | Castillenti |
| 5,147,374 A | 9/1992 | Fernandez |
| 5,158,545 A | 10/1992 | Trudell et al. |
| 5,159,925 A | 11/1992 | Neuwirth et al. |
| 5,163,949 A | 11/1992 | Bonutti |
| 5,176,692 A | 1/1993 | Wilk et al. |
| 5,176,697 A | 1/1993 | Hasson et al. |
| 5,183,463 A | 2/1993 | Debbas |
| 5,188,596 A | 2/1993 | Condon et al. |
| 5,188,630 A | 2/1993 | Christoudias |
| 5,195,507 A | 3/1993 | Bilweis |
| 5,201,742 A | 4/1993 | Hasson |
| 5,201,754 A | 4/1993 | Crittenden et al. |
| 5,209,725 A | 5/1993 | Roth |
| 5,215,526 A | 6/1993 | Deniega et al. |
| 5,222,970 A | 6/1993 | Reeves |
| 5,226,890 A | 7/1993 | Ianniruberto et al. |
| 5,232,446 A | 8/1993 | Arney |
| 5,232,451 A | 8/1993 | Freitas et al. |
| 5,234,454 A | 8/1993 | Bangs |
| 5,250,025 A | 10/1993 | Sosnowski et al. |
| 5,258,026 A | 11/1993 | Johnson et al. |
| 5,269,753 A | 12/1993 | Wilk |
| 5,290,249 A | 3/1994 | Foster et al. |
| 5,308,327 A | 5/1994 | Heaven et al. |
| 5,309,896 A | 5/1994 | Moll et al. |
| 5,314,443 A | 5/1994 | Rudnick |
| 5,318,012 A | 6/1994 | Wilk |
| 5,330,497 A | 7/1994 | Freitas et al. |
| 5,342,307 A | 8/1994 | Euteneuer et al. |
| 5,346,504 A | 9/1994 | Ortiz et al. |
| 5,359,995 A | 11/1994 | Sewell, Jr. |
| 5,361,752 A | 11/1994 | Moll et al. |
| 5,370,134 A | 12/1994 | Chin et al. |
| 5,383,889 A | 1/1995 | Warner et al. |
| 5,397,311 A | 3/1995 | Walker et al. |
| 5,402,772 A | 4/1995 | Moll et al. |
| 5,407,433 A | 4/1995 | Loomas |
| 5,431,173 A | 7/1995 | Chin et al. |
| 5,445,615 A | 8/1995 | Yoon |
| 5,468,248 A | 11/1995 | Chin et al. |
| 5,514,091 A | 5/1996 | Yoon |
| 5,514,153 A | 5/1996 | Bonutti |
| 5,540,658 A | 7/1996 | Evans et al. |
| 5,540,711 A | 7/1996 | Kieturakis et al. |
| 5,607,441 A | 3/1997 | Sierocuk et al. |
| 5,607,443 A | 3/1997 | Kieturakis et al. |
| 5,632,761 A | 5/1997 | Smith et al. |
| 5,656,013 A | 8/1997 | Yoon |
| 5,667,479 A | 9/1997 | Kieturakis |
| 5,667,520 A | 9/1997 | Bonutti |
| 5,704,372 A | 1/1998 | Moll et al. |
| 5,707,382 A | 1/1998 | Sierocuk et al. |
| 5,713,869 A | 2/1998 | Morejon |
| 5,722,986 A | 3/1998 | Smith et al. |
| 5,728,119 A | 3/1998 | Smith et al. |
| 5,730,748 A | 3/1998 | Fogarty et al. |
| 5,730,756 A | 3/1998 | Kieturakis et al. |
| 5,738,628 A | 4/1998 | Sierocuk et al. |
| 5,755,693 A | 5/1998 | Walker et al. |
| 5,762,604 A | 6/1998 | Kieturakis |
| 5,772,680 A | 6/1998 | Kieturakis et al. |
| 5,779,728 A | 7/1998 | Lunsford et al. |
| 5,797,947 A | 8/1998 | Mollenauer |
| 5,803,901 A | 9/1998 | Chin et al. |
| 5,810,867 A | 9/1998 | Zarbatany et al. |
| 5,814,060 A | 9/1998 | Fogarty et al. |
| 5,836,913 A | 11/1998 | Orth et al. |
| 5,836,961 A | 11/1998 | Kieturakis et al. |
| 5,865,802 A | 2/1999 | Yoon et al. |
| 5,893,866 A | 4/1999 | Hermann et al. |
| 5,925,058 A | 7/1999 | Smith et al. |
| 6,361,543 B1 | 3/2002 | Chin et al. |
| 6,368,337 B1 | 4/2002 | Kieturakis et al. |
| 6,375,665 B1 | 4/2002 | Nash et al. |
| 6,379,372 B1 | 4/2002 | Dehdashtian et al. |
| 6,432,121 B1 | 8/2002 | Jervis |
| 6,447,529 B2 | 9/2002 | Fogarty et al. |
| 6,468,205 B1 | 10/2002 | Mollenauer et al. |
| 6,506,200 B1 | 1/2003 | Chin |
| 6,514,272 B1 | 2/2003 | Kieturakis et al. |
| 6,517,514 B1 | 2/2003 | Campbell |
| 6,527,787 B1 | 3/2003 | Fogarty et al. |
| 6,540,764 B1 | 4/2003 | Kieturakis et al. |
| 6,796,960 B2 | 9/2004 | Cioanta et al. |
| 7,083,626 B2 * | 8/2006 | Hart .............. A61B 17/3462 604/167.03 |
| 7,285,112 B2 * | 10/2007 | Stubbs .............. A61B 17/3423 604/23 |
| 7,300,448 B2 | 11/2007 | Criscuolo et al. |
| 7,691,089 B2 | 4/2010 | Gresham |
| 7,967,791 B2 * | 6/2011 | Franer .............. A61B 17/3498 604/167.06 |
| 8,454,645 B2 | 6/2013 | Criscuolo et al. |
| 8,926,508 B2 | 1/2015 | Hotter |

(56) References Cited

U.S. PATENT DOCUMENTS

| | | | | |
|---|---|---|---|---|
| 9,883,942 | B2 * | 2/2018 | Wells | A61B 17/3417 |
| 10,022,149 | B2 * | 7/2018 | Holsten | A61B 17/3462 |
| 10,463,395 | B2 * | 11/2019 | Reid | A61B 17/3498 |
| 2004/0230160 | A1 * | 11/2004 | Blanco | A61B 17/3498 |
| | | | | 604/167.06 |
| 2010/0185139 | A1 | 7/2010 | Stearns et al. | |
| 2010/0268162 | A1 | 10/2010 | Shelton, IV et al. | |
| 2019/0090905 | A1 | 3/2019 | Hall et al. | |

FOREIGN PATENT DOCUMENTS

| | | |
|---|---|---|
| EP | 0880939 A1 | 12/1998 |
| EP | 2177170 A1 | 4/2010 |
| WO | 9206638 A1 | 4/1992 |
| WO | 9218056 A1 | 10/1992 |
| WO | 9221293 A1 | 12/1992 |
| WO | 9221295 A1 | 12/1992 |
| WO | 9309722 A1 | 5/1993 |
| WO | 9721461 A1 | 6/1997 |
| WO | 9912602 A1 | 3/1999 |
| WO | 0126724 A2 | 4/2001 |
| WO | 02096307 A2 | 12/2002 |
| WO | 2004032756 A2 | 4/2004 |
| WO | 2016186905 A1 | 11/2016 |

* cited by examiner

SURGICAL ACCESS DEVICE HAVING PLURAL ZERO CLOSURE VALVES

FIELD

The present disclosure generally relates to surgical instruments for accessing a surgical site. In particular, the present disclosure relates to a surgical access device having plural zero closure valves.

BACKGROUND

In minimally invasive surgical procedures, including endoscopic and laparoscopic surgeries, a surgical access device permits the introduction of a variety of surgical instruments into a body cavity or opening. A surgical access device (e.g., a cannula or an access port) is introduced through an opening in tissue (e.g., a naturally occurring orifice or an incision) to provide access to an underlying surgical site in the body. The opening is typically made using an obturator having a blunt or sharp tip that may be inserted through a passageway of the surgical access device. For example, a cannula has a tube of rigid material with a thin wall construction, through which an obturator may be passed. The obturator is utilized to penetrate a body wall, such as an abdominal wall, or to introduce the surgical access device through the body wall, and is then removed to permit introduction of surgical instruments through the surgical access device to perform the minimally invasive surgical procedure.

Minimally invasive surgical procedures, including both endoscopic and laparoscopic procedures, permit surgery to be performed on organs, tissues, and vessels far removed from an opening within the tissue. In laparoscopic procedures, the abdominal cavity is insufflated with an insufflation gas, e.g., $CO_2$, to create a pneumoperitoneum thereby providing access to the underlying organs. A laparoscopic instrument is introduced through a cannula into the abdominal cavity to perform one or more surgical tasks. The cannula may incorporate a seal to establish a substantially fluid tight seal about the laparoscopic instrument to preserve the integrity of the pneumoperitoneum. The cannula, which is subjected to the pressurized environment, e.g., the pneumoperitoneum, may include an anchor to prevent the cannula from backing out of the opening in the abdominal wall, for example, during withdrawal of the laparoscopic instrument from the cannula.

Recently, laparoscopic peritoneum escape ("LPE") has become a greater operating room concern due to a potentially contaminated patient could infect operating room personnel during or after a surgical procedure as fluids (i.e., liquids or gases) escape the abdomen due to leaks around surgical instruments during insertion and/or removal of the surgical instruments through a surgical access device.

SUMMARY

A surgical access device includes a seal assembly having an instrument seal therein and an upper housing portion coupled to the seal assembly. The upper housing portion includes a first valve that is partially disposed in an upper chamber of the upper housing portion. A lower housing portion is attached to the upper housing portion and includes a second valve that is partially disposed in a lower chamber of the lower housing portion. A valve assembly extends from the upper housing portion and is in fluid communication with the upper chamber. The valve assembly is attachable to a source of insufflation fluid. A tubular member extends from the lower housing portion.

In aspects, an open position of the valve assembly may be configured to introduce insufflation fluid into the upper chamber and define a first pressure therein.

In an aspect, the first pressure may be greater than an ambient pressure of the seal assembly thereby defining a first differential pressure that is capable of urging the first valve towards a closed configuration.

In one aspect, the first pressure may be greater than a second pressure of the lower chamber thereby defining a second differential pressure that is capable of urging the second valve towards an open configuration.

In aspects, a surgical instrument may be inserted through the seal assembly and the first valve. The first differential pressure may be capable of maintaining the first valve in contact with the surgical instrument.

In further aspects, an open position of the valve assembly may be configured to introduce insufflation fluid into the upper chamber and define a first pressure therein. The first pressure may be greater than an ambient pressure in the seal assembly thereby defining a first differential pressure. The first pressure may be greater than a second pressure in the lower chamber thereby defining a second differential pressure. The first differential pressure may be capable of urging the first valve towards a closed position and the second differential pressure may be capable of urging the second valve towards an open position.

In aspects, one of the first or second valves may be a duckbill valve.

In an aspect, the seal assembly may be removably coupled to the upper housing portion.

In another aspect of the present disclosure, a surgical access system has a housing including first and second housing portions with respective first and second chambers. A first valve is partially disposed in the first chamber and a second valve is partially disposed in the second chamber. A valve assembly is connected to the first housing portion and couples a source of fluid with the first chamber. The first chamber has a first pressure with the valve assembly in an open position. A seal assembly is coupled to the first housing portion and has an instrument seal and an ambient pressure therein. The ambient pressure is less than the first pressure thereby defining a first differential pressure that urges the first valve towards a closed position. A tubular member extends from the second housing portion.

In aspects, the first pressure may be greater than a second pressure of the second chamber thereby defining a second differential pressure that urges the second valve towards an open position.

In other aspects, a surgical instrument may be inserted through the seal assembly and the first valve, wherein the first differential pressure maintains contact between the first valve and the surgical instrument.

In an aspect, the first pressure may be greater than a second pressure in the second chamber thereby defining a second differential pressure that urges the second valve towards an open position.

In an aspect, one of the first or second valves may be a duckbill valve.

In one aspect, the seal assembly may be removably coupled to the first housing portion.

In further aspects, the first pressure may be greater than a second pressure in the second chamber thereby defining a second differential pressure that urges the second valve towards an open position thereby facilitating insertion of the surgical instrument through the second valve.

In another aspect of the disclosure, a method of coupling a surgical instrument and a surgical access device includes inserting a surgical instrument into a surgical access device where the surgical access device includes a housing with first and second housing portions and respective first and second chambers. A first valve is partially disposed in the first chamber, a second valve is partially disposed in the second chamber, and a valve assembly is attached to the first housing portion. The valve assembly is fluidly coupled to a source of fluid. A seal assembly is coupled to the first housing portion, and a tubular member extends from the second housing portion. The method also includes opening the valve assembly thereby introducing fluid to the first chamber and defining a first pressure therein. The first pressure is greater than an ambient pressure of the seal assembly thereby defining a first differential pressure that transitions the first valve to a closed position. The first pressure is greater than a second pressure in the second chamber thereby defining a second differential pressure that transitions the second valve to an open position. Additionally, the method includes advancing the surgical instrument through the first and second valves where the first differential pressure maintains contact between the surgical instrument and the first valve. The method also includes withdrawing a distal portion of the surgical instrument into the first chamber where the first differential pressure maintains contact between the surgical instrument and the first valve, while the second differential pressure maintains the second valve in the open position. Further, the method includes withdrawing the distal portion of the surgical instrument into the seal assembly, where the first differential pressure transitions the first valve to the closed position.

In an aspect, inserting the surgical instrument into the surgical access device may include removably coupling the seal assembly to the first housing portion.

In aspects, advancing the surgical instrument through the first and second valves may include inserting the surgical instrument through at least one duckbill valve.

In a further aspect, advancing the surgical instrument through the first and second valves may include inserting the surgical instrument through first and second duckbill valves.

Other features of the disclosure will be appreciated from the following description.

DESCRIPTION OF THE DRAWINGS

The accompanying drawings, which are incorporated in and constitute a part of this specification, illustrate aspects and features of the disclosure and, together with the detailed description below, serve to further explain the disclosure, in which.

DETAILED DESCRIPTION

Figure 1:
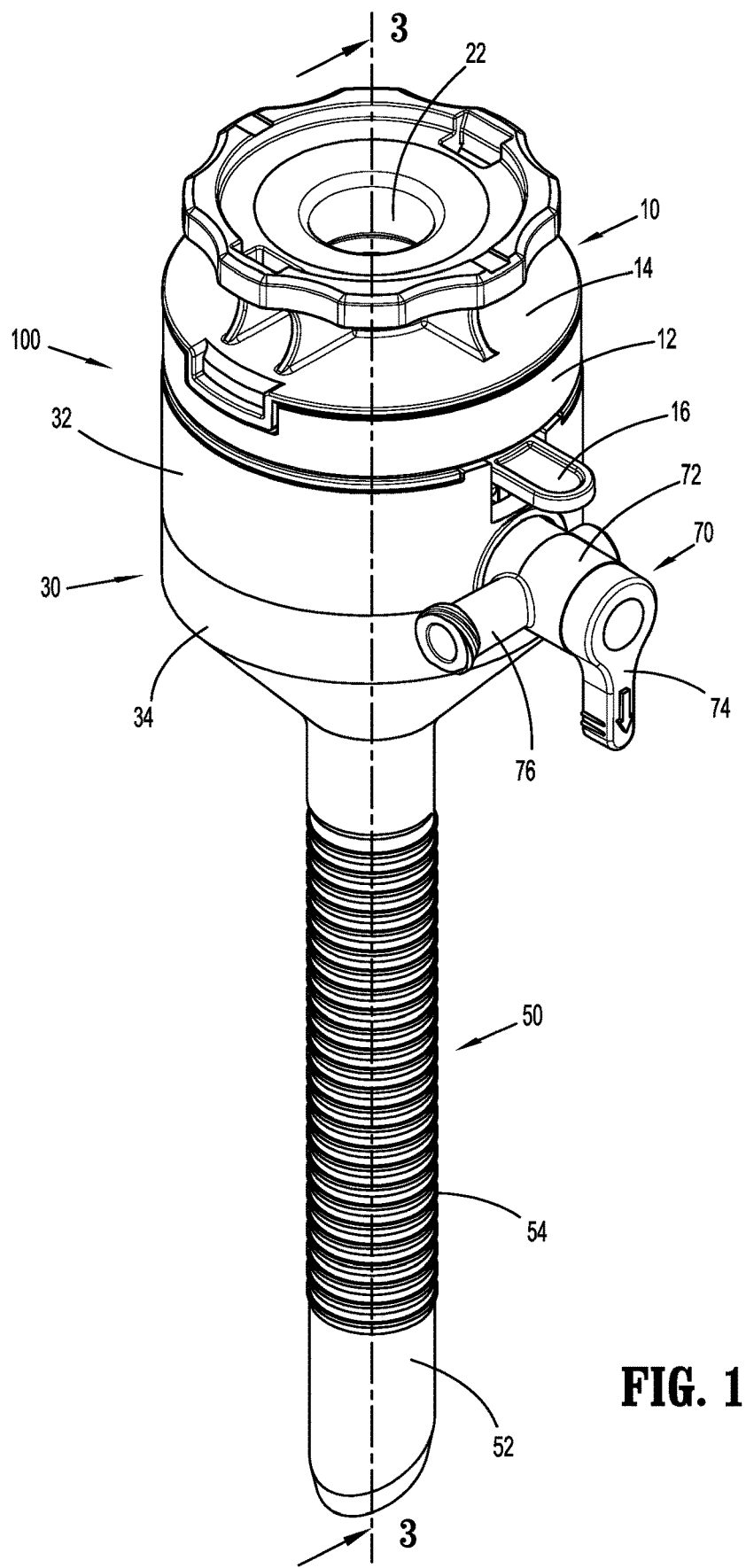
FIG. 1 is a perspective view of a surgical access device according to an aspect of the present disclosure.

Aspects of the disclosure are described hereinbelow with reference to the accompanying drawings; however, it is to be understood that the disclosed aspects are merely exemplary of the disclosure and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure.

Descriptions of technical features of an aspect of the disclosure should typically be considered as available and applicable to other similar features of another aspect of the disclosure. Accordingly, technical features described herein according to one aspect of the disclosure may be applicable to other aspects of the disclosure, and thus duplicative descriptions may be omitted herein. Like reference numerals may refer to like elements throughout the specification and drawings. For a detailed description of the structure and function of exemplary surgical access assemblies, reference may be made to U.S. Pat. Nos. 7,300,448; 7,691,089; and 8,926,508, the entire content of each of which is hereby incorporated by reference herein.

Figure 2:
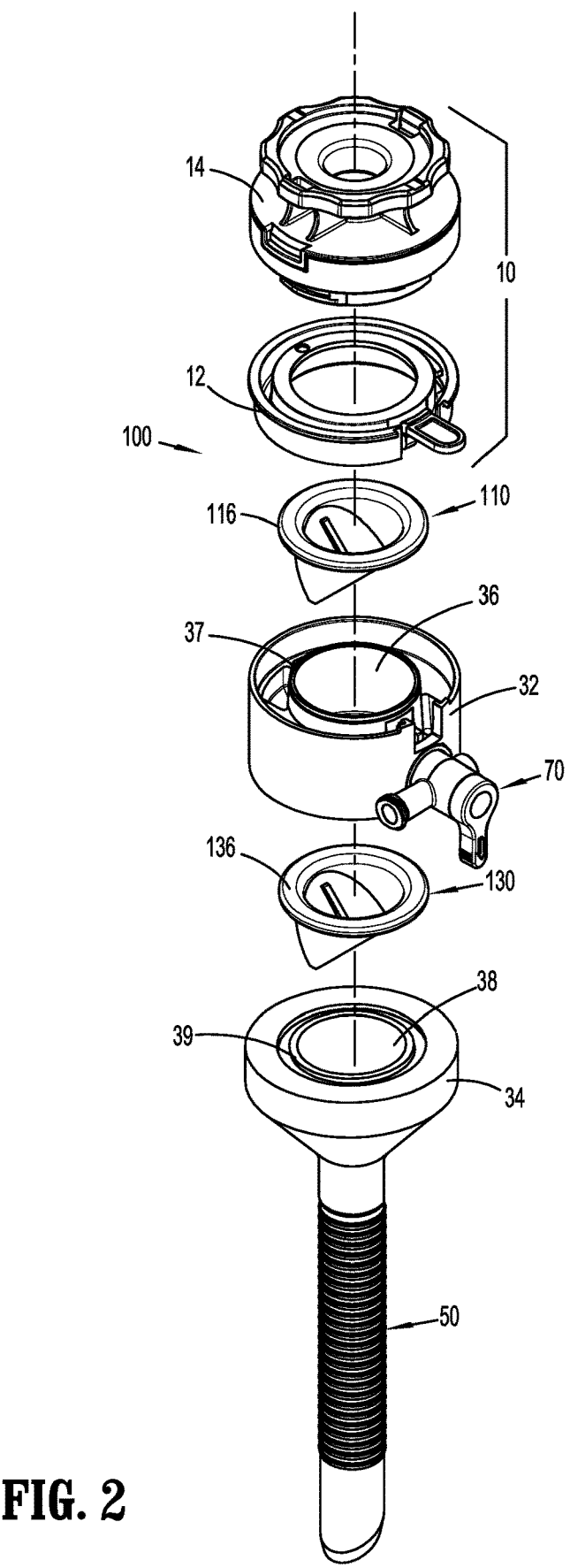
FIG. 2 is an exploded perspective view, with parts separated, of the surgical access device of FIG. 1.
Figure 3:
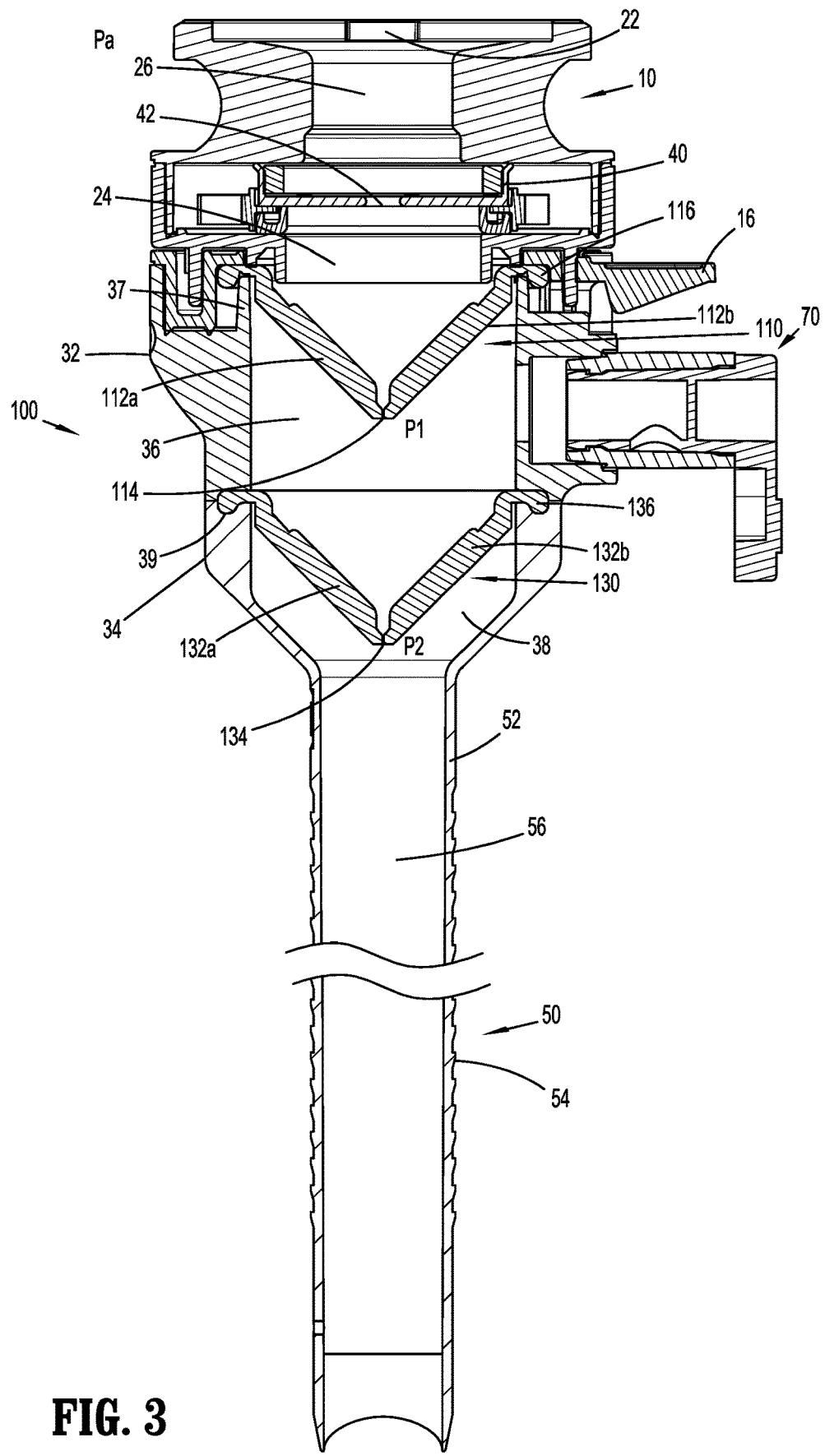
FIG. 3 is a side cross-sectional view of the surgical access device of FIG. 1 taken along section line 3-3.
Figure 4:
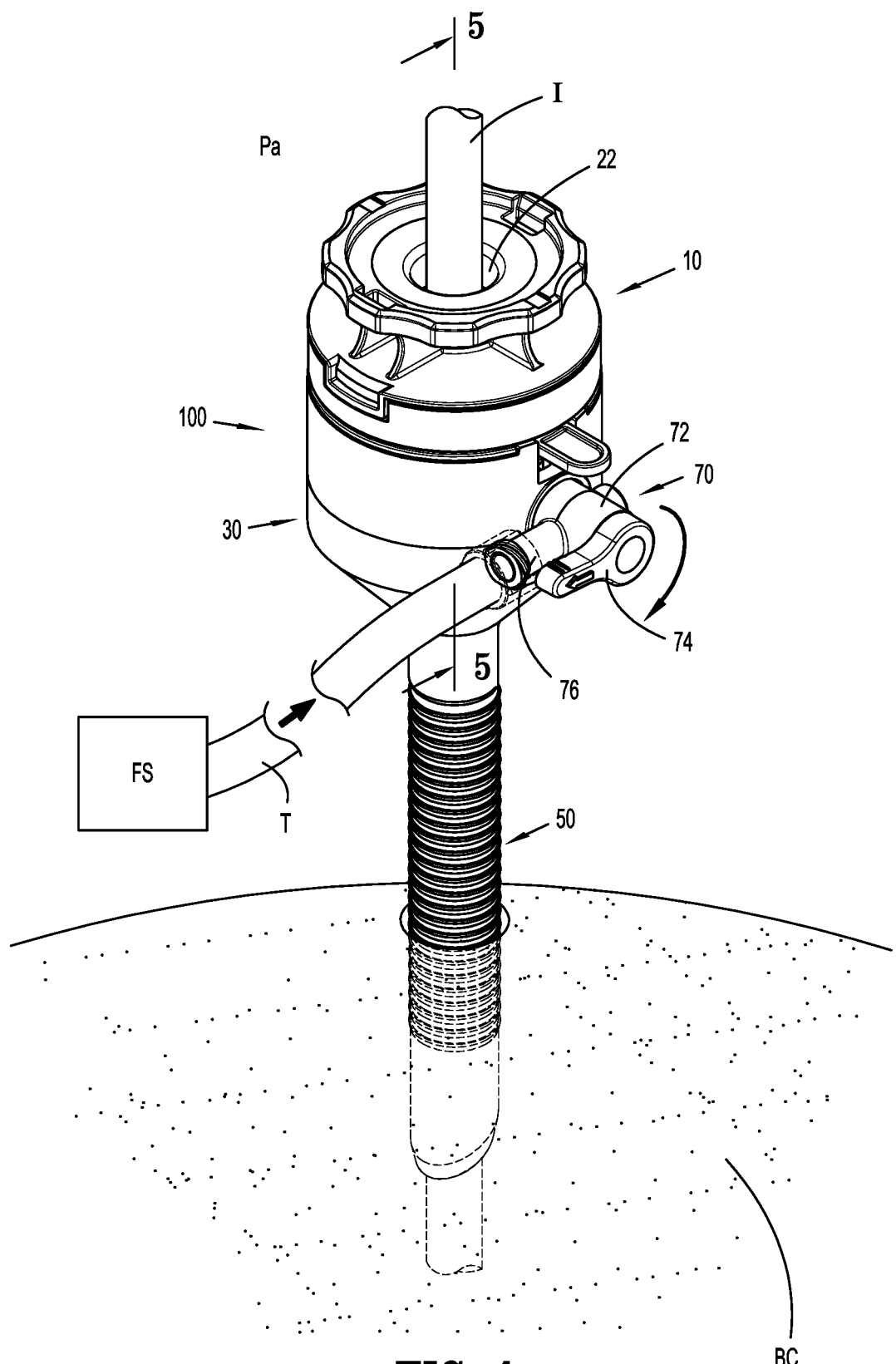
FIG. 4 is a perspective view of the surgical access of FIG. 1 with a surgical instrument inserted therethrough and positioned in body tissue.

With initial reference to FIGS. 1-3, a surgical access device 100 is illustrated. The surgical access device 100 has a seal assembly 10, a housing 30, and a tubular member or cannula 50. The housing 30 includes an upper or first housing portion 32 and a lower or second housing portion 34. The seal assembly 10 is releasably coupled to a proximal portion of the upper housing portion 32 and the cannula 50 extends from the lower housing portion 34. The cannula 50 includes a tubular member 52 and may include ribs or other protrusions 54 along a portion of its length that help stabilize the cannula 50 when it is inserted into tissue (FIG. 4). The seal assembly 10 has a proximal opening 22 and a distal opening 24 (FIG. 3) defining a passage 26 through the seal assembly 10. The seal assembly 10 further includes a base 12 and a body 14 coupled to the base 12. An instrument seal 40 is positioned in the seal assembly 10 and includes a central orifice 42 that sealingly engages a surgical instrument I (FIG. 4) inserted through the passage 26 of the seal assembly 10. When the surgical instrument I is inserted through the central orifice 42, it is engaged with the instrument seal 40 and the instrument seal 40 provides a fluid-tight barrier. The upper housing portion 32 has an upper or first chamber 36 defined therein and a valve assembly 70 extending radially from an outer surface of the upper housing portion 32. The lower housing portion 34 extends distally from the upper housing portion 32 and has a lower or second chamber 38 defined therein. The seal assembly 10, the upper housing portion 32, the lower housing portion 34, and the cannula 50 are formed from a suitable biocompatible polymeric material (e.g., polycarbonate).

A first valve 110 is disposed in the upper housing portion 32. In particular, a flange 116 of the first valve 110 engages a rim 37 of the upper housing portion 32 thereby supporting the first valve 110 in the upper housing portion 32. The first valve 110 is a conical elastomeric membrane, such as a duckbill or zero-closure valve fabricated from a resilient material, such as, for example, rubber, etc. The first valve 110 is flexible for resilient reception of the surgical instrument I and maintaining seal integrity between the first chamber 36 and the ambient environment. The first valve 110 includes first and second flaps 112a, 112b that are inwardly biased towards a contact region 114 so as to form a seal. First and second flaps 112a, 112b define the contact region 114 that is configured for receiving the surgical instrument I therethrough. The contact region 114 permits passage of the surgical instrument I through the first valve 110 whereby the first and second flaps 112a, 112b form a substantial seal with a shaft of the surgical instrument I when it is inserted therethrough. In the absence of the surgical instrument I being inserted through the first valve 110, the contact region 114 forms a fluid tight seal that isolates the first chamber 36 from the ambient environment.

A second valve 130 is disposed in the lower housing portion 34. In particular, a flange 136 of the second valve 130 engages a groove 39 of the lower housing portion 34 thereby supporting the second valve 130 in the lower housing portion 34. The second valve 130 is a conical elastomeric membrane, such as a duckbill or zero-closure valve fabricated from a resilient material, such as, for example, rubber, etc. The second valve 130 is flexible for resilient reception of the surgical instrument I and maintaining seal integrity between the first chamber 36 and the second chamber 38. The second valve 130 includes first and second flaps 132a, 132b that are inwardly biased towards a contact region 134 so as to form a seal. First and second flaps 132a, 132b define the contact region 134 that is configured for receiving the surgical instrument I therethrough. The contact region 134 permits passage of the surgical instrument I through the second valve 130 whereby the first and second flaps 132a, 132b form a substantial seal with a shaft of the surgical instrument I when it is inserted therethrough. In the absence of the surgical instrument I being inserted through the second valve 130, the contact region 134 forms a fluid tight seal that isolates the second chamber 38 from a lumen 56 (FIG. 4) of the cannula 50.

Figure 5:
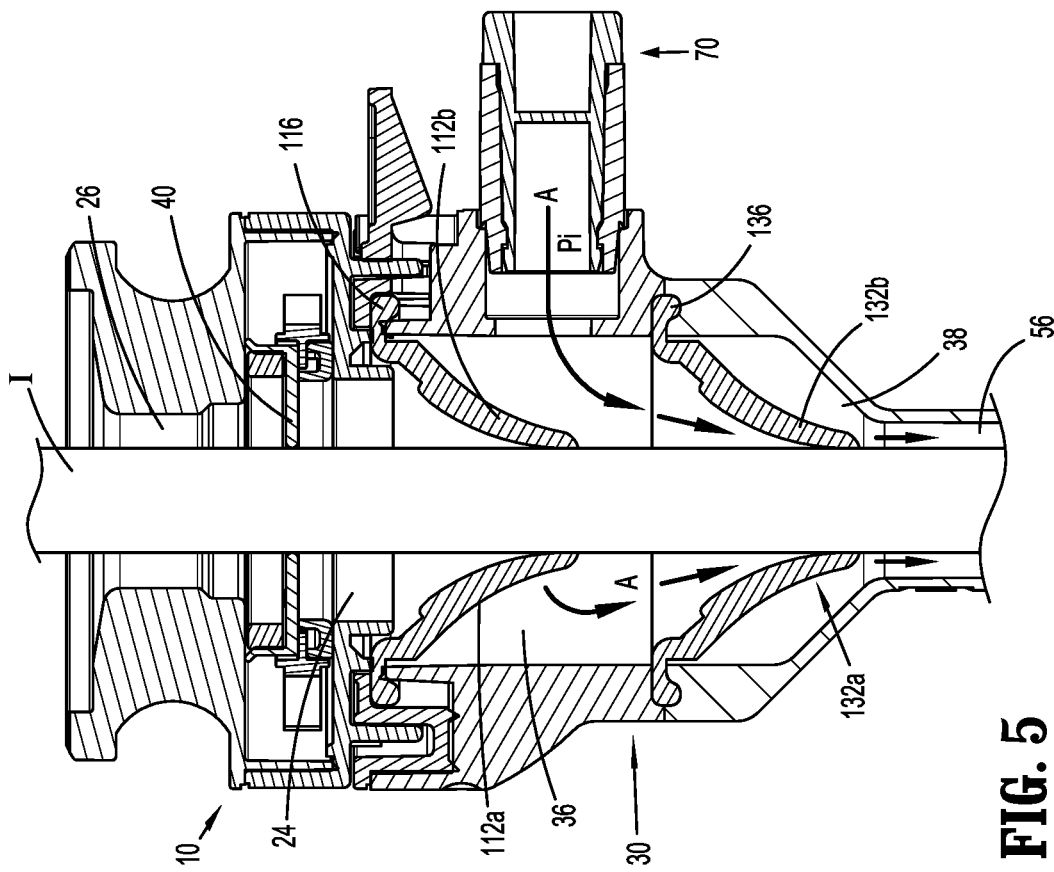
FIG. 5 is a side cross-sectional view of the surgical access device of FIG. 4 taken along section line 5-5 with the surgical instrument engaging first and second zero closure valves.

With reference to FIGS. 3-5, the ambient air surrounding the surgical access device 100 has an ambient pressure Pa that is exerted on an exterior of the surgical access device 100. At sea level, the ambient pressure is approximately 14.7 psi or 101.325 kPa. A first differential pressure ($\Delta P$) is defined by the difference between the ambient pressure $P_a$ and a first pressure $P_1$ of the first chamber 36. If the first pressure $P_1$ is greater than the ambient pressure $P_a$, then the first $\Delta P$ is positive. A negative first $\Delta P$ exists when the ambient pressure $P_a$ is greater than the first pressure $P_1$. Similarly, a second $\Delta P$ is defined by the difference between the first pressure $P_1$ and a second pressure $P_2$ of the second chamber 38, which is substantially equal to a pressure present in the lumen 56 of the cannula 50. If the second pressure $P_2$ is greater than the first pressure $P_1$, then the second $\Delta P$ is positive. A negative second $\Delta P$ exists when the first pressure $P_1$ is greater than the second pressure $P_2$. In the initial state, the ambient pressure $P_a$, the first pressure $P_1$, and the second pressure $P_2$ are all substantially equal and the first and second valves 110, 130 remain in a closed configuration.

The base 12 of the seal assembly 10 is releasably attached to the upper housing portion 32 of the housing 30. A tab 16 is integrally formed with the seal assembly 10 and is configured for resilient movement relative to the upper housing portion 32 such that the tab 16 is movable in a distal direction relative to the seal assembly 10. Moving the tab 16 distally permits a user to rotate the seal assembly 10 relative to the upper housing portion 32 for removal of the seal assembly 10 from the surgical access device 100. Attachment of the seal assembly 10 to the upper housing portion 32 of the surgical access device 100 involves rotating the seal assembly 10 relative to the upper housing portion 32 in an opposite direction. An example of a seal assembly coupled to a housing of a surgical access device is described in commonly owned U.S. Pat. No. 10,022,149, the entire content of which is incorporated herein by reference.

The valve assembly 70 includes a body 72, a valve handle 74, and a port 76. The valve assembly 76 may be a stopcock style valve. The valve handle 74 is rotatable between an open position (FIG. 4) that allows fluid flow into or out of the valve assembly 70 and a closed position (FIG. 1) that inhibits fluid flow into or out of the valve assembly 70. The port 76 may have a fitting such as a luer fitting and is configured to allow the valve assembly 70 to be coupled to a source of insufflation fluid FS via tube T that has an insufflation pressure $P_i$ that is greater than the ambient pressure $P_a$. When the pressurized insufflation fluid is introduced into the first chamber 36 via the valve assembly 70, the first pressure $P_1$ of the first chamber is also greater than the ambient pressure $P_a$ (i.e., positive first $\Delta P$) thereby maintaining the first valve 110 in the closed configuration. This further limits any fluids that might escape from the surgical access assembly 100 through the first valve 110 to the environment surrounding the surgical access device 100 (e.g., operating room). Additionally, the first pressure $P_1$ of the first chamber 36 is now greater than the second pressure $P_2$ of the second chamber 38 and the second $\Delta P$ is negative thereby urging the second valve 130 towards an open configuration and allowing the insufflation fluid to flow into the second chamber 36 through the lumen 56 of the cannula 50 and into the body cavity BC (e.g., a surgical working space) as indicated by the arrows A.

Figure 6:
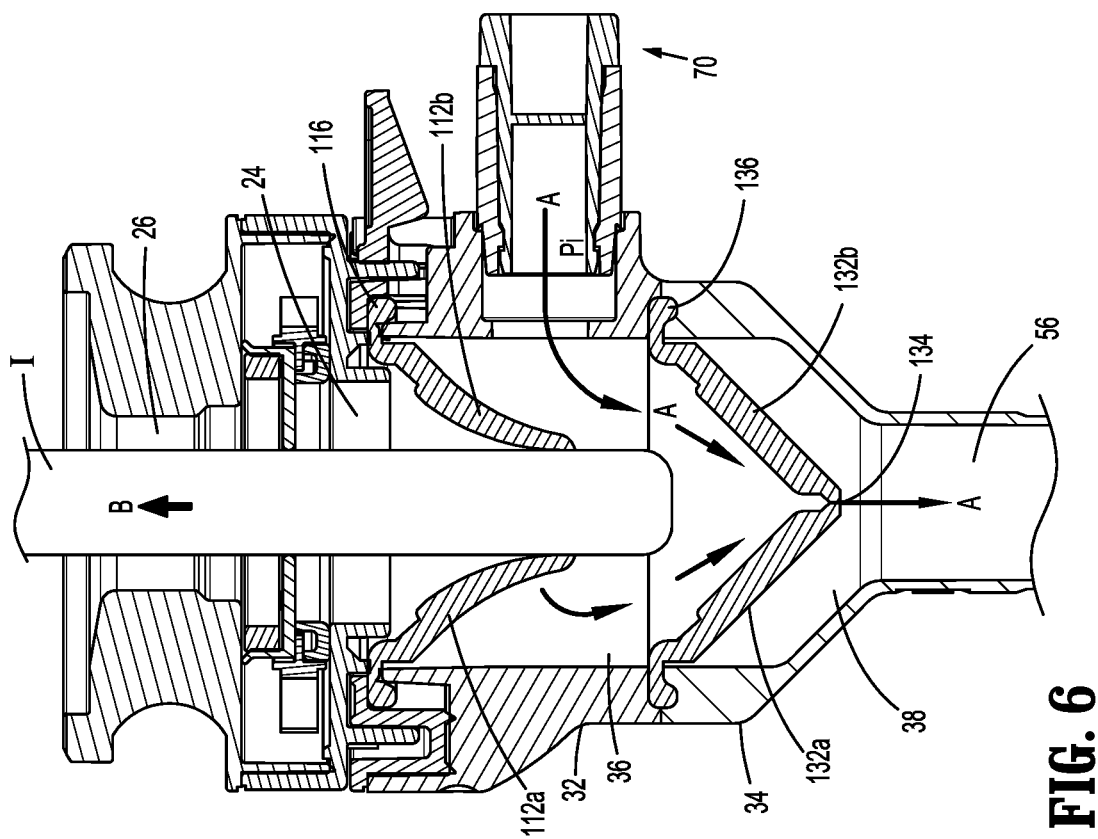
FIG. 6 is a side cross-sectional view of the surgical access device of FIG. 5 with the surgical instrument partially withdrawn and engaging the first zero closure valve.
Figure 7:
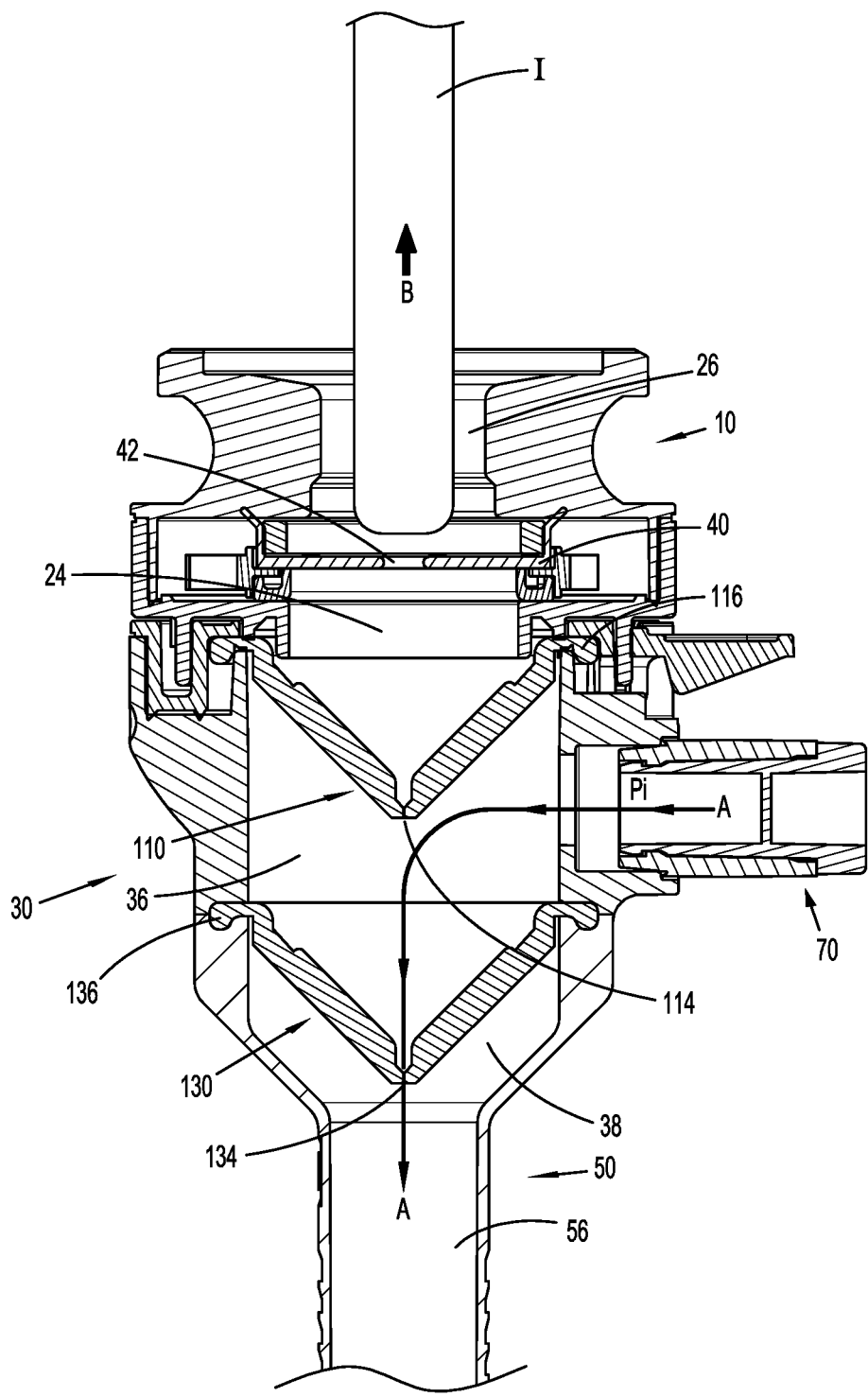
FIG. 7 is a side cross-sectional view of the surgical access device of FIG. 5 with the surgical instrument partially withdrawn and disengaged from the first and second zero closure valves.

Referring now to FIGS. 5-7, insertion and removal of the surgical instrument I with respect to the surgical access device 100 are illustrated. Initially, as seen in FIG. 5, the surgical instrument I is inserted through the proximal opening 22 (FIG. 4) of the seal assembly 10, through the central orifice 42 of the instrument seal 40, through the contact regions 114, 134 of the first and second valves 110, 130, and into the lumen 56 of the cannula 50. The resilient nature of the flaps 112a, 112b of the first valve 110 maintain contact between the flaps 112a, 112b and an outer surface of the surgical instrument I thereby defining a fluid-tight boundary. The fluid-tight boundary between the first valve 110 and the surgical instrument I is augmented by the insufflation fluid entering the first chamber 36 from the valve assembly 70. As the insufflation fluid enters the first chamber 36, the first chamber 36 has a higher pressure than the ambient pressure $P_a$ in the seal assembly 10 and the positive first $\Delta P$ urges the flaps 112a, 112b of the first valve 110 towards the closed configuration thereby maintaining contact between the flaps 112a, 112b and the surgical instrument I. This arrangement inhibits fluids (e.g., liquids or gases) from entering the seal assembly 10 from the first chamber 36. Additionally, the first pressure $P_1$ in the first chamber 36 is greater than the second pressure $P_2$ in the second chamber 38 and the lumen 56 of the cannula 50 thereby defining the negative second $\Delta P$. The negative second $\Delta P$ urges the flaps 132a, 132b of the second valve 130 towards the open configuration. As such, the insufflation fluid flows along the outer surface of the surgical instrument I and through the contact region 134 of the second valve 110 and into the lumen 56 of the cannula 50 as shown by arrows A. This flow path further limits any fluids from exiting the surgical access device 100 through the proximal opening 22 of the seal assembly 10.

In FIG. 6, the surgical instrument I is being withdrawn in the direction of arrow B from the surgical access device 100 while insufflation fluid is still being supplied to the surgical access device 100 through the valve assembly 70 as shown by arrows A. Similar to the arrangement in FIG. 5, the flaps 112a, 112b of the first valve 110 are in contact with the outer surface of the surgical instrument I and are urged towards the closed configuration by the positive first ΔP thereby maintaining contact between the flaps 112a, 112b and the surgical instrument I to inhibit any fluids exiting the surgical access device 100 through the seal assembly 10. Additionally, the negative second ΔP keeps the flaps 132a, 132b of the second valve 130 from closing thereby allowing fluid flow from the first chamber 36 through the second valve 130 and into the second chamber 38 as well as the lumen 56 of the cannula 50 as shown by arrows A. The instrument seal 40 also maintains contact with the surgical instrument I (FIGS. 5 and 6) to inhibit any fluid flow past the instrument seal I towards the proximal opening 22.

As seen in FIG. 7, the surgical instrument I has been withdrawn to a point where a distal tip of the surgical instrument I is positioned proximally of the instrument seal 40 in the seal assembly 10. As such, the instrument seal 40 no longer inhibits fluid flow in either direction through the central orifice 42 of the instrument seal 40. As the valve handle 74 of the valve assembly 70 is still in the open position, insufflation fluid is still being supplied to the surgical access device 100 as shown by arrows A. In particular, the insufflation fluid enters the first chamber with a higher pressure $P_i$ than the ambient pressure $P_a$ in the seal assembly 10 maintaining the positive first ΔP. The positive first ΔP continues to urge the flaps 112a, 112b of the first valve 110 towards a closed configuration augmenting the flaps 112a, 112b bias towards the closed configuration. In combination, the bias of the flaps 112a, 112b and the positive first ΔP inhibit proximal fluid flow across the first valve 110. Concurrently, the first pressure $P_1$ in the first chamber 36 is greater than the second pressure $P_2$ in the second chamber 38 and maintains the negative second ΔP. The negative second ΔP urges the flaps 132a, 132b of the second valve 130 apart allowing insufflation fluid to flow from the first chamber 36, through the second valve 130, into the second chamber 38, and into the lumen 56 of the cannula 50. The positive pressure $P_1$ of the first chamber 36 relative to the ambient pressure $P_a$ inhibits LPE of fluids in the surgical access device 100. Further, since the pressure $P_1$ in the first chamber 36 is greater than the pressure $P_2$ in the second chamber 38, which is equal to the pressure in the lumen 56 of the cannula 50, any LPE of fluids is directed towards the body cavity BC (e.g., surgical access site) rather than potentially escaping into the environment surrounding the surgical access device 100 (e.g., operating room).

Persons skilled in the art will understand that the devices and methods specifically described herein and illustrated in the accompanying drawings are non-limiting. It is envisioned that the elements and features may be combined with the elements and features of another without departing from the scope of the disclosure. As well, one skilled in the art will appreciate further features and advantages of the disclosure.

What is claimed is:

1. A surgical access device comprising:
   a seal assembly having an instrument seal;
   an upper housing portion coupled to the seal assembly;
   a first valve partially disposed in an upper chamber of the upper housing portion;
   a lower housing portion comprising a proximal end attached to the upper housing portion and comprising an opposite distal end, the lower housing portion comprising a conical neck narrowing an inner diameter of the lower housing portion from a first inner diameter at the proximal end to a second, smaller inner diameter at the distal end;
   a second valve partially disposed in a lower chamber of the lower housing portion and supported by the lower housing portion proximal of the conical neck, the first valve and the second valve being duckbill valves, the second valve spanning the first inner diameter and including a circumferential flange and first and second flaps that form a seal at a contact region;
   a valve assembly extending from the upper housing portion and in fluid communication with the upper chamber, the valve assembly attachable to a source of insufflation fluid; and
   a cannula extending from the lower housing portion, the cannula defining a lumen having a lumen diameter less than the first inner diameter of the lower housing portion,
   wherein the contact region forms a distal-most end of the second valve that is disposed proximal to the cannula when the circumferential flange is disposed between the upper housing portion and the proximal end of the lower housing portion.

2. The surgical access device of claim 1, wherein an open position of the valve assembly is configured to introduce insufflation fluid into the upper chamber and define a first pressure of the upper chamber.

3. The surgical access device of claim 2, wherein the first pressure is greater than an ambient pressure of the seal assembly thereby defining a first differential pressure that is capable of urging the first valve towards a closed configuration.

4. The surgical access device of claim 3, further including a surgical instrument inserted through the seal assembly and the first valve, wherein the first differential pressure is capable of maintaining the first valve in contact with the surgical instrument.

5. The surgical access device of claim 2, wherein the first pressure is greater than a second pressure of the lower chamber thereby defining a second differential pressure that is capable of urging the second valve towards an open configuration.

6. The surgical access device of claim 1, wherein an open position of the valve assembly is configured to introduce insufflation fluid into the upper chamber and define a first pressure of the upper chamber, the first pressure greater than an ambient pressure in the seal assembly thereby defining a first differential pressure, the first pressure greater than a second pressure in the lower chamber thereby defining a second differential pressure, the first differential pressure capable of urging the first valve towards a closed position and the second differential pressure capable of urging the second valve towards an open position.

7. The surgical access device of claim 6, further including a surgical instrument inserted through the seal assembly and the first valve, wherein the first differential pressure is capable of maintaining the first valve in contact with the surgical instrument.

8. The surgical access device of claim 1, wherein the seal assembly is removably coupled to the upper housing portion.

9. The surgical access device of claim 1, wherein the first valve and the second valve are symmetric duckbill valves.

10. A surgical access system comprising:
a housing including a first housing portion having a first chamber and a second housing portion having a second chamber, the second housing portion further comprising a proximal end and an opposite distal end and a conical neck narrowing an inner diameter of the second housing portion from a first inner diameter at the proximal end to a second, smaller inner diameter at the distal end;
a first valve partially disposed in the first chamber;
a second valve partially disposed in the second chamber, the first valve and the second valve being duckbill valves, the second valve supported by the second housing portion proximal of the conical neck, the second valve spanning the first inner diameter and including a circumferential flange and first and second flaps that form a seal at a contact region;
a valve assembly connected to the first housing portion, the valve assembly coupling a source of fluid with the first chamber, the first chamber having a first pressure with the valve assembly in an open position;
a seal assembly coupled to the first housing portion, the seal assembly having an instrument seal and an ambient pressure therein, the ambient pressure less than the first pressure thereby defining a first differential pressure that urges the first valve towards a closed position; and
a cannula extending from the distal end of the second housing portion, the cannula defining a lumen having a lumen diameter less than the first inner diameter of the second housing portion,
wherein the contact region forms a distal-most end of the second valve that is disposed proximal to the cannula when the circumferential flange is disposed between the first housing portion and the proximal end of the second housing portion.

11. The surgical access system of claim 10, wherein the first pressure is greater than a second pressure of the second chamber thereby defining a second differential pressure that urges the second valve towards an open position.

12. The surgical access system of claim 10, further including a surgical instrument inserted through the seal assembly and the first valve, wherein the first differential pressure maintains contact between the first valve and the surgical instrument.

13. The surgical access system of claim 12, wherein the first pressure is greater than a second pressure in the second chamber thereby defining a second differential pressure that urges the second valve towards an open position thereby facilitating insertion of the surgical instrument through the second valve.

14. The surgical access system of claim 10, wherein the seal assembly is removably coupled to the first housing portion.

15. A surgical access device comprising:
a seal assembly having an instrument seal;
a housing including an upper housing portion and a lower housing portion, the lower housing portion comprising a proximal end, a distal end, and a conical neck narrowing an inner diameter of the lower housing portion from a first inner diameter at the proximal end to a second, smaller inner diameter at the distal end;
a first valve disposed in an upper chamber of the upper housing portion, the upper chamber having a first pressure;
a second valve disposed in a lower chamber of the lower housing portion and supported by the lower housing portion proximal of the conical neck, the lower chamber having a second pressure, wherein when the second pressure is greater than the first pressure, the second valve is urged towards a closed position, and wherein the second valve spans the first inner diameter and includes a circumferential flange and first and second flaps that form a seal at a contact region;
a valve coupled to the upper housing portion and in fluid communication with the upper chamber, the valve attachable to a source of fluid; and
a cannula extending from the lower housing portion, the cannula defining a lumen having a lumen diameter less than the first inner diameter of the lower housing portion,
wherein the contact region forms a distal-most end of the second valve that is disposed proximal to the cannula when the circumferential flange is disposed between the upper housing portion and the proximal end of the lower housing portion.

16. The surgical access device of claim 15, wherein an open position of the valve is configured to introduce insufflation fluid into the upper chamber.

17. The surgical access device of claim 15, wherein the first pressure is greater than an ambient pressure thereby defining a first differential pressure that urges the first valve towards a closed position.

18. The surgical access device of claim 17, further including a surgical instrument inserted through the seal assembly and the first valve, wherein the first differential pressure is capable of maintaining the first valve in contact with the surgical instrument.

19. The surgical access device of claim 15, wherein the first valve and the second valve are proximal of the cannula.

20. The surgical access device of claim 15, wherein the first valve and the second valve are symmetric duckbill valves.

* * * * *